(12) United States Patent
Kawamura et al.

(10) Patent No.: US 6,426,329 B1
(45) Date of Patent: Jul. 30, 2002

(54) IMMUNOSUPPRESSANT ACTIVITY OF INSULIN-LIKE GROWTH FACTOR I (IGF-I)

(75) Inventors: Ikuo Kawamura, Hirakata; Mariko Ohta, Kobe; Shigeru Takeshita, Mino, all of (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/581,236

(22) PCT Filed: Dec. 11, 1998

(86) PCT No.: PCT/JP98/05602

§ 371 (c)(1),
(2), (4) Date: Jun. 23, 2000

(87) PCT Pub. No.: WO99/33487

PCT Pub. Date: Jul. 8, 1999

(30) Foreign Application Priority Data

Dec. 24, 1997 (JP) .............................................. 9-354936
Aug. 27, 1998 (JP) ........................................... 10-241514

(51) Int. Cl.[7] ........................ A61K 38/00; A61K 38/13; A61K 38/18; A01N 25/00

(52) U.S. Cl. ............................. 514/12; 514/3; 514/893; 930/120

(58) Field of Search ............................. 424/93.1, 93.21, 424/93.7, 184.1, 278.1; 514/294, 326, 411, 3, 12, 893; 930/120

(56) References Cited

U.S. PATENT DOCUMENTS

| 5,196,437 A | * | 3/1993 | Starzl et al. ................. 514/294 |
| 5,534,493 A | | 7/1996 | Gluckman et al. |
| 5,597,563 A | * | 1/1997 | Beschorner ................ 424/93.7 |

FOREIGN PATENT DOCUMENTS

JP       3185268        5/2001

* cited by examiner

*Primary Examiner*—Jeffrey Stucker
*Assistant Examiner*—Jegatheesan Seharaseyon
(74) *Attorney, Agent, or Firm*—Oblon, Spivak, McClelland, Maier & Neustadt, P.C.

(57) ABSTRACT

The invention provides a composition for improving an action of an immunosuppressant, comprising insulin-like growth factor I or its analog as an active ingredient.

15 Claims, No Drawings

US 6,426,329 B1

IMMUNOSUPPRESSANT ACTIVITY OF INSULIN-LIKE GROWTH FACTOR I (IGF-I)

TECHNICAL FIELD

This invention relates to an immunosuppressant agonists and finds application in the field of health care. More particularly, this invention relates to a pharmaceutical composition for improving the action of an immunosuppressant which comprises insulin-like growth factor I (IGF-I) or its analog as an active ingredient and to the use thereof. Furthermore,.the invention relates to enhancement of IGF-I production with a macrolide compound.

DISCLOSURE OF INVENTION

The inventors of this invention found after intensive research that insulin-like growth factor I (IGF-I) inclusive of its analog has a strong effect for improving an action of immunosuppressants and that the immunosuppressive macrolide compound has a potent IGF-I production enhancing action, and have accordingly developed this invention.

IGF-I or its analog for use in this invention includes native IGF-I's , products resulting from the fractional purification thereof, and IGF-I's produced by recombinant DNA (c f. EP-A-155655, for instance), peptide synthesis, cell culture or other technology, for example those derived from the human, bovine or other mammal. The analog of IGF-I includes various IGF-I-active muteins available upon partial change, i.e. insertion, substitution, deletion and/or addition, in the amino acid sequence of IGF-I and chemical modification products such as O-glucosylated IGF-I (WO 90/02198). As a preferred example of such analog of IGF-I, there can be mentioned the muteins resulting from the deletion or omission of 1~5 amino acids from the N-terminus of the sequence as disclosed in WO 89/05822. To avoid undesirable immune responses, the use of IGF-I of the human origin or an analog thereof is preferred.

The "action of an immunosuppressant" in the context of this invention means the action that is expressed when a substance generally called immunosuppressant is administered to animals inclusive of man, specifically the immunosuppressive action, prophylactic/therapeutic action on diseases of the liver as described in U.S. Pat. No. 5,196,437, and/or liver anagenesis accelerating action.

More particularly, the "action of an immunosuppressant" includes the therapeutic or prophylactic action on the following conditions or diseases.

(1) The rejection of transplanted organs or tissues such as heart, kidney, liver, bone marrow, skin, etc.
(2) The graft-versus-host reaction in a bone marrow transplantation.
(3) Autoimmune diseases such as rheumatoid arthritis, systemic lupus erythematosus, Hashimoto's thyroiditis, multiple sclerosis, myasthenia gravis, insulin-dependent diabetes mellitus, uveitis, etc.
(4) Postoperative complications in partial hepatectomy.
(5) Acute hepatonecrosis caused by toxins, viral hepatitis, shock or anoxia, or of unknown origin.
(6) Immunogenic diseases of the liver, e.g. chronic autoimmune diseases of the liver such as autoimmune hepatitis, primary biliary cirrhosis, sclerosing cholangitis, etc.
(7) Chronic diseases of the liver other than autoimmune hepatitis, such as virus B hepatitis, non-A, non-B hepatitis, cirrhosis (e.g. alcoholic cirrhosis, cirrhosis of unknown origin, etc.) and so on.

As a corollary, the preferred "action improving the action of an immunosuppressant" is the improvement and/or enhancement of the therapy or prophylaxis in the above-mentioned conditions or diseases.

The preferred other "action of an immunosuppressant" to be improved is the side effect of any substance known as an immunosuppressant and the "improvement of its action" is the alleviation or inhibition of the side effect. By way of illustration, immunosuppressants classed as "cyclosporins", particularly cyclosporin A (CsA), are known to cause various adverse reactions such as bone loss, suppression of choleresis, suppression of bile acid secretion, and cholestatic symptoms, and the immunosuppressant agonists of this invention alleviates or inhibits such side effects.

The "composition for improving an action of immunosuppressant" of this invention can be administered, either together with an immunosuppressant at one and the same time or independently at a different time, by an administration route judiciously selected from among the conventional routes (intravenous, intramuscular, subcutaneous, intraperitoneal, rectal, nasal, etc.). The amount of the active ingredient IGF-I or IGF-I analog in the composition for improving an action of the immunosuppressant need only be just enough to bring about the expected effect and is dependent on the patient's age and the route of administration, among other conditions. Usually, however, the daily dose-of about 1~100 mg/kg, preferably about 1~20 mg/kg, as IGF-I, on an adult basis, can be administered in a single dose or in divided doses.

Regarding the dosage form of said "composition for improving an action of an immunosuppressant", a suitable dosage form can be selected with reference to the route of administration to be used, from among various solid forms such as tablets, capsules, powders, granules, fine granules, troches, pills and suppositories, various semisolid forms such as ointments and creams, liquid forms such as solutions, suspensions, syrups and elixirs, and liposomes. Such pharmaceutical preparations can be manufactured by the routine procedures optionally employing a pharmaceutical carrier, excipient, stabilizer and other pharmaceutically acceptable additives. For use as an injection, the composition can be provided in the form of a solid preparation (e.g. lyophilized product) for extemporaneous reconstitution. Among such pharmaceutical preparations, there can be reckoned the freeze-dried preparation described in EP-A-440989 and the nasal. preparation described in JP Kokai H5–58877.

When the composition for improving an action of an immunosuppressant of this invention is to be administered together with an immunosuppressant at the same time, the IGF-I or IGF-I analog and the immunosuppressant may be formulated together, optionally with the aid of a pharmaceutical carrier, excipient, stabilizer and/or other pharmaceutically acceptable additives, in the routine manner and the resulting composition be put to use.

The immunosuppressant whose action is to be improved by this invention and the immunosuppressant to be used for the production of said composition comprising an IGF-I or its analog and an immunosuppressant may each be any substance having immunosuppressive activity.

Macrolide compound such as FK506, ascomycin derivatives, rapamycin derivatives, and so on; cyclosporins; and so on can be exemplified as the preferable examples.

More particular examples of the macrolide compounds, the tricyclic compound of the following formula (I) or pharmaceutically acceptable salts thereof can be exemplified.

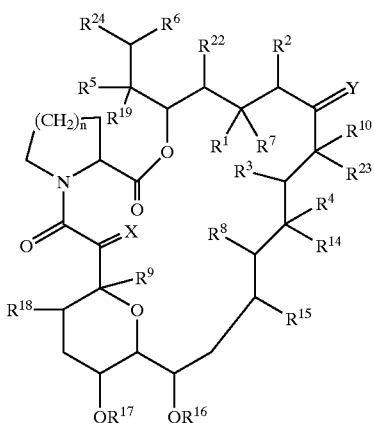

(I)

(wherein each of adjacent pairs of $R^1$ and $R^2$, $R^3$ and $R^4$, and $R^5$ and $R^6$ independently
(a) is two adjacent hydrogen atoms, but $R^2$ may also be an alkyl group or
(b) may form another bond formed between the carbon atoms to which they are attached;

$R^7$ is a hydrogen atom, a hydroxy group, a protected hydroxy group, or an alkoxy group, or an oxo group together with $R^1$;

$R^8$ and $R^9$ are independently a hydrogen atom or a hydroxy group;

$R^{10}$ is a hydrogen atom, an alkyl group, an alkyl group substituted by one or more hydroxy groups, an alkenyl group, an alkenyl group substituted by one or more hydroxy groups, or an alkyl group substituted by an oxo group;

X is an oxo group, (a hydrogen atom and a hydroxy group) (a hydrogen atom and a hydrogen atom), or a group represented by the formula —CH$_2$O—;

Y is an oxo group, (a hydrogen atom and a hydroxy group) (a hydrogen atom and a hydrogen atom), or a group represented by the formula N—NR$^{11}$R$^{12}$ or N—OR$^{13}$;

$R^{11}$ and $R^{11}$ are independently a hydrogen atom, an alkyl group, an aryl group or a tosyl group;

$R^{13}$, $R^{14}$, $R^{15}$, $R^{16}$, $R^{17}$, $R^{18}$, $R^{19}$, $R^{22}$ and $R^{23}$ are independently a hydrogen atom or an alkyl group;

$R^{24}$ is an optionally substituted ring system which may contain one or more heteroatoms;

n is an integer of 1 or 2; and in addition to the above definitions, Y, $R^{10}$ and $R^{23}$, together with the carbon atoms to which they are attached, may represent a saturated or unsaturated 5- or 6-membered nitrogen, sulfur and/or oxygen containing heterocyclic ring optionally substituted by one or more groups selected from the group consisting of an alkyl, a hydroxy, an alkoxy, a benzyl, a group of the formula —CH$_2$Se(C$_6$H$_5$), and an alkyl substituted by one or more hydroxy groups.

Preferable $R^{24}$ may be cyclo(C$_{5-7}$)alkyl group which may have suitable substituents, and the following ones can be exemplified.
(a) a 3,4-di-oxo-cyclohexyl group;
(b) a 3-R$^{20}$-4-R$^{21}$-cyclohexyl group,
in which $R^{20}$ is hydroxy, an alkoxy group, or a —OCH$_2$OCH$_2$CH$_2$OCH$_3$ group, and $R^{21}$ is hydroxy, —OCN, an alkoxy group, a heteroaryloxy which may be substituted by suitable substituent(s), a
—OCH$_2$OCH$_2$CH$_2$OCH$_3$ group, a protected hydroxy group, chloro, bromo, iodo, aminooxalyloxy, an azido group, p-tolyloxythiocarbonyloxy,
or R$^{25}$R$^{26}$CHCOO—,
in which $R^{25}$ is optionally protected hydroxy or protected amino, and
$R^{26}$ is hydrogen or methyl, or
$R^{20}$ and $R^{21}$ together form an oxygen atom in an epoxide ring; or (c) cyclopentyl group substituted by methoxymethyl, optionally protected hydroxymethyl, acyloxymethyl (in which the acyl moiety optionally contains either a dimethylamino group which may be quaternized, or a carboxy group which may be esterified), one or more amino and/or hydroxy groups which may be protected, or aminooxalyloxymethyl. A preferred example is a 2-formyl-cyclopentyl group.

The definitions used in the above general formula (I) and the specific and preferred examples thereof are now explained and set forth in detail.

The term "lower" means, unless otherwise indicated, a group having 1 to 6 carbon atoms.

Preferable examples of the "alkyl groups" and an alkyl moiety of the "alkoxy group" include a straight or branched chain aliphatic hydrocarbon residue, for example, a lower alkyl group such as methyl, ethyl, propyl, isopropyl, butyl, isobutyl, pentyl, neopentyl and hexyl.

Preferable examples of the "alkenyl groups" include a straight or branched chain aliphatic hydrocarbon residue having one double-bond, for example, a lower alkenyl group such as vinyl, propenyl (e.g., allyl group), butenyl, methylpropenyl, pentenyl and hexenyl.

Preferable examples of the "aryl groups" include phenyl, tolyl, xylyl, cumenyl, mesityl and naphthyl.

Preferable protective groups in the "protected hydroxy groups" and the "protected amino" are 1-(lower alkylthio)-(lower)alkyl group such as a lower alkylthiomethyl group (e.g., methylthiomethyl, ethylthiomethyl, propylthiomethyl, isopropylthiomethyl, butylthiomethyl, isobutylthiomethyl, hexylthiomethyl, etc.), more preferably C$_1$–C$_4$ alkylthiomethyl group, most preferably methylthiomethyl group;

trisubstituted silyl group such as a tri(lower)alkylsilyl (e.g., trimethylsilyl, triethylsilyl, tributylsilyl, tert-butyldimethylsilyl, tri-tert-butylsilyl, etc.) or lower alkyl-diarylsilyl (e.g., methyldiphenylsilyl, ethyldiphenylsilyl, propyldiphenylsilyl, tert-butyldiphenyl-silyl, etc.), more preferably tri(C$_1$–C$_4$) alkylsilyl group and C$_1$–C$_4$ alkyldiphenylsilyl group, most preferably tert-butyldimethylsilyl group and tert-butyldiphenylsilyl group; and an acyl group such as an aliphatic, aromatic acyl group or an aliphatic acyl group substituted by an aromatic group, which are derived from a carboxylic acid, sulfonic acid or carbamic acid.

Examples of the aliphatic acyl groups include a lower alkanoyl group optionally having one or more suitable substituents such as carboxy, e.g., formyl, acetyl, propionyl, butyryl, isobutyryl, valeryl, isovaleryl, pivaloyl, hexanoyl, carboxyacetyl, carboxypropionyl, carboxybutyryl, carboxyhexanoyl, etc.; a cyclo(lower)alkoxy(lower)alkanoyl group optionally having one or more suitable substituents such as lower alkyl, e.g., cyclopropyloxyacetyl, cyclobutyloxypropionyl, cycloheptyloxybutyryl, menthyloxyacetyl, menthyloxypropionyl, menthyloxybutyryl, menthyloxypentanoyl, menthyloxyhexanoyl, etc.; a camphorsulfonyl group; or a lower alkylcarbamoyl group having one or more suitable substituents such as carboxy or protected carboxy, for example, carboxy(lower)alkylcarbamoyl group (e.g., carboxymethylcarbamoyl, carboxyethylcarbamoyl, carboxypropylcarbamoyl, carboxybutylcarbamoyl, carboxypentylcarbamoyl, carboxyhexylcarbamoyl, etc.), tri-(lower)alkylsilyl(lower)alkoxycarbonyl(lower)alkylcarbamoyl group (e.g., trimethylsilylmethoxycarbonylethylcarbamoyl, trimethylsilylethoxycarbonylpropylcarbamoyl, triethylsilylethoxycarbonylpropylcarbamoyl, tert-butyldimethylsilylethoxycarbonylpropylcarbamoyl, trimethylsilylpropoxycarbonylbutylcarbamoyl, etc.) and so on.

Examples of the aromatic acyl groups include an aroyl group optionally having one or more suitable substituents such as nitro, e.g., benzoyl, toluoyl, xyloyl, naphthoyl, nitrobenzoyl, dinitrobenzoyl, nitronaphthoyl, etc.; and an arenesulfonyl group optionally having one or more suitable substituents such as halogen, e.g., benzenesulfonyl, toluenesulfonyl, xylenesulfonyl, naphthalenesulfonyl, fluorobenzenesulfonyl, chlorobenzenesulfonyl, bromobenzenesulfonyl, iodobenzenesulfonyl, etc.

Examples of the aliphatic acyl groups substituted by an aromatic group include ar(lower)alkanoyl group optionally having one or more suitable substituents such as lower alkoxy or trihalo(lower)alkyl, e.g., phenylacetyl, phenylpropionyl, phenylbutyryl, 2-trifluoromethyl-2-methoxy-2-phenylacetyl, 2-ethyl-2-trifluoromethyl-2-phenylacetyl, 2-trifluoromethyl-2-propoxy-2-phenylacetyl, etc.

More preferable acyl groups among the aforesaid acyl groups are $C_1$–$C_4$ alkanoyl group optionally having carboxy, cyclo ($C_5$–$C_6$) alkoxy ($C_1$–$C_4$) alkanoyl group having two ($C_1$–$C_4$) alkyls at the cycloalkyl moiety, camphorsulfonyl group, carboxy-($C_1$–$C_4$) alkylcarbamoyl group, tri($C_1$–$C_4$) alkylsilyl($C_1$–$C_4$)-alkoxycarbonyl ($C_1$–C4)alkylcarbamoyl group, benzoyl group optionally having one or two nitro groups, benzenesulfonyl group having halogen, or phenyl ($C_1$–$C_4$)alkanoyl group having $C_1$–$C_4$ alkoxy and trihalo ($C_1$–$C_4$) alkyl group. Among these, the most preferable ones are acetyl, carboxypropionyl, menthyloxyacetyl, camphorsulfonyl, benzoyl, nitrobenzoyl, dinitrobenzoyl, iodobenzenesulfonyl and 2-trifluoromethyl-2-methoxy-2-phenylacetyl.

Preferable examples of the "5- or 6-membered nitrogen, sulfur and/or oxygen containing heterocyclic ring" include a pyrrolyl group and a tetrahydrofuryl group. "A heteroaryl which may be substituted by suitable substituent (s)" moiety of the "heteroaryloxy which may be substituted by suitable substituent(s)" may be the one exemplified for $R^1$ of the compound of the formula of EP-A-532,088, with preference given to 1-hydroxyethyl-indol-5-yl, the disclosure of which is incorporated herein by reference.

The ticyclic compounds (I) and its pharmaceutically acceptable salt for use in accordance with this invention are well known to have excellent immunosuppressive activity, antimicrobial activity and other pharmacological activities and, as such, be of value for the treatment or prevention of rejection reactions by transplantation of organs or tissues, graft-vs-host diseases, autoimmune diseases, and infectious diseases [EP-A-0184162, EP-A-0323042, EP-A-423714, EP-A-427680, EP-A-465426, EP-A-480623, EP-A-532088, EP-A-532089, EP-A-569337, EP-A-626385, WO89/05303, WO93/05058, WO96/31514, WO91/13889, WO91/19495, WO93/5059, etc.], the disclosures of which are incorporated herein by reference.

Particularly, the compounds which are designated as FR900506 (=FK506), FR900520 (ascomycin), FR900523, and FR900525 are products produced by microorganisms of the genus Streptomyces, such as *Streptomyces tsukubaensis* No. 9993 [deposited with National Institute of Bioscience and Human Technology Agency of Industrial Science and Technology (formerly Fermentation Research Institute Agency of Industrial Science and Technology ), at 1–3, Higashi 1-chome, Tsukuba-shi, Ibaraki, Japan, date of deposit Oct. 5, 1984, accession number FERM BP-927] or *Streptomyces hygroscopicus* subsp. yakushimaensis No. 7238 [deposited with National Institute of Bioscience and Human Technology Agency of Industrial Science and Technology (formerly Fermentation Research Institute Agency of Industrial Science and Technology ), at 1–3, Higashi 1-chome, Tsukuba-shi, Ibaraki, Japan, date of deposit Jan. 12, 1985, accession number FERM BP-928][EP-A-0184162]. The FK506 (general name: tacrolimus) of the following chemical formula, in particular, is a representative compound.

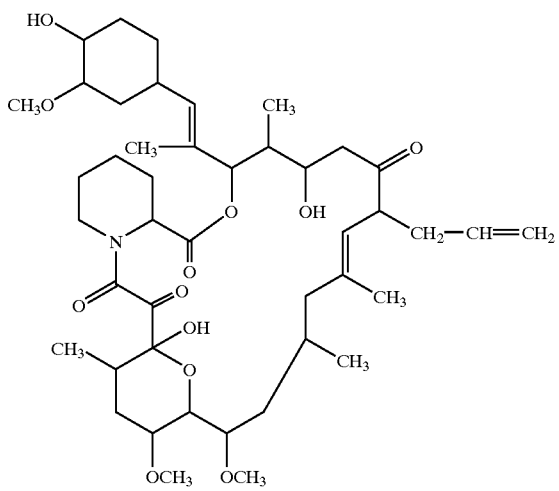

Chemical name: 17-allyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo [22.3.1.0$^{4,9}$] octacos-18-ene-2,3,10,16-tetraone In the present invention, FK506 includes and may be in the form of its salt, isomer, or hydrate.

The preferred examples of the tricyclic compounds (I) are the ones, wherein each of adjacent pairs of $R^3$ and $R^4$ or $R^5$ and $R^6$ independently form another bond formed between the carbon atoms to which they are attached;
each of $R^8$ and $R^{23}$; is independently a hydrogen atom;
$R^9$ is a hydroxy group;
$R^{10}$ is a methyl group, an ethyl group, a propyl group or an allyl group;
X is (a hydrogen atom and a hydrogen atom) or an oxo group;
Y is an oxo group;
each of $R^{14}$, $R^{15}$, $R^{16}$, $R^{17}$, $R^{18}$, $R^{19}$, and $R^{22}$ is a methyl group; $R^{24}$ is a 3-$R^{20}$-4-$R^{21}$-cyclohexyl group,
in which $R^{20}$ is hydroxy, an alkoxy group, or a —OCH$_2$OCH$_2$CH$_2$OCH$_3$ group, and
$R^{21}$ is hydroxy, —OCN, an alkoxy group, a heteroaryloxy which may be substituted by suitable substituent(s), a —CH,OCH,CH$_2$OCH3 group, a protected hydroxy group, chloro, bromo, iodo, aminooxalyloxy, an azido group, p-tolyloxythiocarbonyloxy, or $R^{25}R^{26}$CHCOO—,
in which $R^{25}$is optionally protected hydroxy or protected amino, and
$R^{26}$ is hydrogen or methyl, or
$R^{20}$ and $R^{21}$ together form an oxygen atom in an epoxide ring; and
n is an integer of 1 or 2.

The most preferable tricyclic compounds(I) is, in addition to FK506, ascomycin derivatives such as halogenated-ascomycin (e.g., 33-epi-chloro-33-desoxyascomycin), which is disclosed in EP 427,680, example 66a.

As the other preferable example of the macrolides as immunosuppressants, rapamycin [THE MERCK INDEX (12th edition) , No. 8288] and its derivatives can be exemplified. Preferred example of the derivatives is an O-substituted derivative in which the hydroxy in position 40 of formula A illustrated at page 1 of WO 95/16691, incorporated herein by reference, is replaced by—OR, in which $R_1$ is hydroxyalkyl, hydroalkoxyalkyl, acylaminoalkyl and aminoalkyl; for example 40-O-(2-hydroxy)ethyl-rapamycin, 40-O-(3-hydroxy)propyl-rapamycin, 40-O-[2-2-hydroxy)ethoxy]ethyl-rapamycin and 40-O-(2-acetaminoethyl)-rapamycin. These O-substituted derivatives may be produced by reacting rapamycin (or dihydro or deoxo-rapamycin) with an organic radical attached to a leaving group (for example RX where R is the organic radical which is desired as the O-substituent, such as an alkyl, allyl, or benzyl moiety, and X is a leaving group such as $CCl_3C(NH)O$ or $CF_3SO_3$) under suitable reaction conditions. The conditions may be acidic or neutral conditions, for example in the presence of an acid like trifluoromethanesulfonic acid, camphorsulfonic acid, p-toluenesulfonic acid or their respective pyridinium or substituted pyridinium salts when X is $CCl_3C(NH)O$ or in the presence of a base like pyridine, a substituted pyridine, diisopropylethylamine or pentamethylpiperidine when X is $CF_3SO_3$. The most preferable one is 40-O-(2-hydroxy)ethyl rapamycin, which is disclosed in WO94/09010, the disclosure of which is incorporated herein by reference.

The tricyclic compounds(I), and rapamycin and its derivatives, have a similar basic structure, i.e., tricyclic macrolide structure, and at least one of the similar biological properties (for example, immunosupressive activity).

The tricyclic compounds(I), and rapamycin and its derivatives, may be in a form of its salt, which includes conventional non-toxic and pharmaceutically acceptable salt such as the salt with inorganic or organic bases, specifically, an alkali metal salt such as sodium salt and potassium salt, an alkali earth metal salt such as calcium salt and magnesium salt, an ammonium salt and an amine salt such as triethylamine salt and N-benzyl-N-methylamine salt.

With respect to the macrolide compounds, it is to be understood that there may be conformers and one or more stereoisomers such as optical and geometrical isomers due to asymmetric carbon atom(s) or double bond(s), and such conformers and isomers are also included within the scope of the present invention. And further, the macrolide compounds can be in the form of a solvate, which is included within the scope of the present invention. The solvate preferably include a hydrate and an ethanolate.

Further example of the immunosuppressant is cyclosporin and its derivatives such as cyclosporin A, B, C, D, E, F, G, etc, which are shown in THE MERCK INDEX (12th edition), No. 2821, U.S. Pat. Nos. 4,117,118, 4,215,199, 4,288,431, 4,388,307, Helv. Chim. Acta. 60, 1568(1977) and 65, 1655(1982), Transplant. Proc. 17, 1362(1985), and so on. Among which, the most preferable one is cyclosporin A. The disclosures of the above references are incorporated herein.

While the dosage of therapeutically effective amount of the immunosuppressants of the present invention varies from and also depends upon the age and condition of each individual patient to be treated, a daily dose of about 0.01–1000 mg, preferably 0.1–500 mg and more preferably 0.5–100 mg. of the active ingredient is generally given for treating diseases, and an average single dose of about 0.1 mg, 0.5 mg, 1 mg, 5 mg, 10 mg, 50 mg, 100 mg, 250 mg and 500 mg is generally administered.

In addition, this invention relates to enhancement of IGF-I production by an immunosuppressive macrolide compound. It is well known that IGF-I and its analogs have useful pharmacologic actions and are of value for the treatment of dwarfism, promotion of growth of mammary gland soft tissue, acceleration of bone growth, and treatment or prevention of renal diseases. Therefore, administration of a macrolide compound having IGF-I producing activity promotes the production of IGF-I and brings about benefits in the treatment or prevention of such IGF-I-responsive diseases.

The preferred macrolide compound includes the aforementioned tricyclo compound (I) and its pharmaceutically acceptable salt, with FK506 being particularly preferred.

In further aspects, this invention relates to a choleretic composition, bile acid secretion promoting composition or therapeutic composition for cholestasis, which comprises a compound having IGF-I producing activity, such as said macrolide compound, as an active ingredient, to a related method of therapy, and to a method of use thereof.

As mentioned above, IGF-I is not only useful for the therapy of dwarfism and promotion of bone growth but also has choleretic and bile acid secretion promoting actions. Therefore, it can be expected to be effective in the therapy of cholestasis as well. Therefore, by administering a compound having IGF-I producing activity to thereby induce IGF-I production in vivo, the beneficial effect ascribable to IGF-I can be attained without resort to the direct administration of IGF-I.

The "IGF- I-producing compound" in the context of this invention means any compound that is capable of producing IGF-I but is preferably the macrolide compound mentioned hereinbefore, more preferably said tricyclo compound (I) and its pharmaceutically acceptable salt. Particularly preferred is FK506. The IGF-I -producing compound can be put to use in the form of neat compound or in the form of a composition prepared by formulating the compound with an optional pharmaceutical carrier, excipient, stabilizer and/or other pharmaceutically acceptable additives in the routine manner.

In this invention, such IGF-I -producing compound as an active ingredient can be used in the form of a solid, semisolid or liquid pharmaceutical preparation containing the same in admixture with an organic or inorganic carrier or excipient suitable for external application, intestinal administration, intramuscular administration or (other non-) oral administration. This active ingredient can be mixed with the conventional nontoxic pharmaceutically acceptable carrier for preparation of tablets, pellets, capsules, suppositories, solutions (e.g. in saline), emulsions, suspensions (e.g. in olive oil) and other dosage forms. The carrier which can be used includes solid, semisolid or liquid pharmaceutically acceptable carriers such as water, glucose, lactose, gum arabic, gelatin, mannitol, starch paste, magnesium trisilicate, talc, corn starch, keratin, colloidal silica, potato starch, urea and so on. In addition, various excipients, stabilizers, thickeners, coloring agents and flavors can also be added. The active ingredient is caused to occur in such a pharmaceutical composition at an effective concentration insuring the desired effect depending on the course or stage of disease. Such pharmaceutical compositions can be produced by the established technology.

For application of the IGF-I -producing compound according to this invention to human beings, it is preferably administered orally, parenterally, intestinally, or intramuscularly. Particularly when the IGF-I -producing compound is a macrolide compound, the therapeutically effective dose is judiciously selected according to the individual patient's age, status of disease and other factors, and in terms of the daily dose of the compound may generally be about 0.01~1000 mg, preferably 0.1~500 mg, more preferably 0.5~100 mg. Usually, the average unit dose is about 0.1 mg, 0.5 mg, 1 mg, 5 mg, 10 mg, 50 mg, 100 mg, 250 mg or 500 mg.

The following examples describe advantageous features of this invention, it being to be understood that these examples are intended to describe the invention in further detail and should by no means be construed as defining the scope of the invention.

As the baseline secretions, the average of the values at 2 points of time immediately preceding drug administration was used. The IGF-I monotherapy group was comprised of 4 rats and the other three groups were respectively comprised of 5 rats.

(2) Results

The results are shown in Table 1.

TABLE 1

Anticholeretic action of CsA and antagonizing action of IGF-I

Bile secretions (ml/30 min; % of preadministration baseline in parentheses

| | n | Before administration | 0~30 min | 30~60 min | 60~90 min | 90~120 min | 120~150 min | 150~180 min |
|---|---|---|---|---|---|---|---|---|
| Saline | 5 | 0.32 ± 0.05 (100) | 0.32 ± 0.05 (100) | 0.31 ± 0.04 (97) | 0.31 ± 0.04 (97) | 0.29 ± 0.04 (91) | 0.29 ± 0.04 (91) | 0.29 ± 0.04 (91) |
| IGF-I 10 mg/kg | 4 | 0.33 ± 0.03 (100) | 0.36 ± 0.03 (109) | 0.40 ± 0.02 (121) | 0.41 ± 0.03 (124) | 0.39 ± 0.02 (118) | 0.40 ± 0.02 (121) | 0.39 ± 0.02 (118) |
| CsA 10 mg/kg | 5 | 0.37 ± 0.01 (100) | 0.34 ± 0.02 (92) | 0.35 ± 0.02 (95) | 0.34 ± 0.02 (92) | 0.32 ± 0.02 (86) | 0.31 ± 0.01 (84) | 0.30 ± 0.01 (83) |
| IGF-I + CsA | 5 | 0.38 ± 0.01 (100) | 0.37 ± 0.02 (97) | 0.42 ± 0.02 (111) | 0.42 ± 0.02 (111) | 0.42 ± 0.02 (111) | 0.42 ± 0.01 (111) | 0.42 ± 0.01 (111) |

Mean ± S.E.

EXAMPLE 1

IGF-I Producing Action of FK506

(1) Method

Male SD rats aged 6 weeks were orally dosed with FK506 once daily for 7 consecutive days, and at 0.5 hour following the final dose, the liver and blood were isolated. The blood IGF-I concentration was measured by acid-ethanol extraction and subsequent assay with a rat IGF-I RIA kit (DSL). The hepatic IGF-I level was measured by acetic acid extraction and subsequent assay with the rat IGF-I RIA kit. Five rats per group were used.

(2) Results

Administration of FK506 in doses of 1 and 10 mg/kg increased the concentration of IGF-I in the liver by 28% and 26%, respectively, and the blood concentration of IGF-I by 14% and 11%, respectively. FK506 was considered to express IGF-I producing activity in the liver.

EXAMPLE 2

Anticholeretic Action of CsA and Antagonizing Action of IGF-I (1) Method

Using male SD rats (7 weeks old) under urethane anesthesia (1.2 g/5 ml/kg), a midline incision was made in the abdominal region. Ligation was performed at the lower part of the common bile duct and a polyethylene tube (PE10, Intramedics) was inserted from above and ligated in position. The bile was thus withdrawn extracorporeally and pooled. The rat was kept warm on a hot plate at 37° C. and the volume of the bile withdrawn was measured at 30-min intervals. After confirmation that the baseline secretions became substantially steady, CsA was administered intravenously (10 mg/2 ml/kg) or IGF-I subcutaneously (10 mg/2 ml/kg), or both drugs were administered concurrently (CsA: intravenous; IGF-I: subcutaneous). IGF-I was dissolved in saline. As to CsA, Sandoz's Sandimmune Inj. (250 mg/5 ml vial) was diluted with saline. Rats in the control group received saline both intravenously and subcutaneously. The bile was collected up to 180 min after drug administration.

EXAMPLE 3

Choleretic Action of FK506 and Synergistic Action of IGF-I (1) Method

Using male SD rats (6 weeks old) under urethane anesthesia (1.2 g/5 ml/kg), a midline incision was made in the abdominal region. Ligation was performed at the lower part of the common bile duct and a polyethylene tube (PE10, Intramedics) was inserted from above and ligated in position. The bile was thus withdrawn extracorporeally and pooled. The rat was kept warm on a hot plate at 37° C. and the volume of the bile withdrawn-was measured at 30-min intervals. After confirmation that the baseline secretions became substantially steady, FK506 was administered intravenously (10 mg/1 ml/kg) or IGF-I subcutaneously (10 mg/2 ml/kg), or both drugs were administered concurrently (FK506: intravenous; IGF-I: subcutaneous). IGF-I was dissolved in saline. As to FK506, FK506 Inj. (1P mg/1 ml vial) was used. Rats in the control group received saline both intravenously and subcutaneously. The bile was collected up to 180min after medication. As the baseline secretions, the average of the values at 2 points of time immediately preceding drug administration was used. The control group and the IGF-I monotherapy group were respectively comprised of 9 rats and the FK506 monotherapy group and the combination therapy group were respectively comprised of 10 rats.

(2) Results

The results are shown in Table 2.

TABLE 2

Choleretic action of FK506 and synergistic action of IGF-I

Bile secretions (ml/30 min: % of preadministration baseline in parentheses)

|  | n | Before administration | 0~30 min | 30~60 min | 60~90 min | 90~120 min | 120~150 min | 150~180 min |
|---|---|---|---|---|---|---|---|---|
| Saline | 9 | 0.35 ± 0.02 (100) | 0.34 ± 0.01 (97) | 0.33 ± 0.01 (94) | 0.33 ± 0.01 (94) | 0.32 ± 0.01 (91) | 0.32 ± 0.01 (91) | 0.31 ± 0.01 (89) |
| IGF-I 10 mg/kg | 9 | 0.35 ± 0.01 (100) | 0.38 ± 0.01 (109) | 0.41 ± 0.01 (117) | 0.42 ± 0.02 (120) | 0.42 ± 0.02 (120) | 0.43 ± 0.02 (123) | 0.40 ± 0.02 (114) |
| CsA 10 mg/kg | 10 | 0.36 ± 0.02 (100) | 0.44 ± 0.02 (122) | 0.43 ± 0.02 (119) | 0.41 ± 0.02 (114) | 0.39 ± 0.02 (108) | 0.38 ± 0.02 (106) | 0.38 ± 0.02 (106) |
| IGF-I + CsA | 10 | 0.34 ± 0.01 (100) | 0.46 ± 0.02 (135) | 0.52 ± 0.02 (153) | 0.51 ± 0.01 (150) | 0.48 ± 0.02 (141) | 0.48 ± 0.01 (141) | 0.45 ± 0.01 (132) |

Mean ± S.E.

It is apparent from the above data that whereas CsA suppresses choleresis, FK506 has a choleretic action and that IGF-I enhances choleresis when used in combination with whichever of the two drugs. Therefore, IGF-I is useful, whether in monotherapy or in combination therapy with an immunosuppressant, as a therapeutic drug for cholestasis which develops in the liver graft, for instance.

Disclosures in the patents, patent applications and other literature referred to in the instant application are hereby incorporated in this specification by reference.

What is claimed is:

1. A method of alleviating or inhibiting side effect caused by cyclosporin A, which is suppression of choleresis, suppression of bile acid secretion, and/or cholestasis, comprising:

administering an effective amount of insulin-like growth factor I to a subject.

2. The method of claim 1, wherein the insulin-like growth factor I thereof and cyclosporin A are administered simultaneously.

3. The method of claim 1, wherein the insulin-like growth factor I and cyclosporin A are administered independently.

4. The method of claim 1, Therein the subject is a human.

5. The method of claim 1, wherein a daily dose of 1 to 20 mg/kg per day of the insulin-like growth factor I is administered to the subject.

6. The method of claim 1, wherein the side effect is suppression of choleresis.

7. The method of claim 1, wherein the side effect is suppression of bile acid secretion.

8. The method of claim 1, wherein the side effect is cholestasis.

9. The method of claim 1, wherein the insulin-like growth factor I is administered intravenously.

10. The method of claim 1, wherein the insulin-like growth factor I is administered intramuscularly.

11. The method of claim 1, wherein the insulin-like growth factor I is administered subcutaneously.

12. The method of claim 1, wherein the insulin-like growth factor I is administered intraperitoneally.

13. The method of claim 1, wherein the insulin-like growth factor I is administered rectally.

14. The method of claim 1, wherein the insulin-like growth factor I is administered nasally.

15. The method of claim 1, wherein the insulin-like growth factor I is administered orally.

* * * * *